US010534202B2

(12) United States Patent
Yajima et al.

(10) Patent No.: US 10,534,202 B2
(45) Date of Patent: Jan. 14, 2020

(54) WEARABLE DEVICE AND ELECTRICITY SUPPLY SYSTEM

(71) Applicant: SONY CORPORATION, Tokyo (JP)

(72) Inventors: Masakazu Yajima, Tokyo (JP);
Takatoshi Nakamura, Tokyo (JP);
Masanori Iwasaki, Tokyo (JP);
Takayuki Hirabayashi, Tokyo (JP);
Itaru Kawakami, Tokyo (JP)

(73) Assignee: SONY CORPORATION, Tokyo (JP)

( * ) Notice: Subject to any disclaimer, the term of this patent is extended or adjusted under 35 U.S.C. 154(b) by 390 days.

(21) Appl. No.: 14/902,960

(22) PCT Filed: Aug. 4, 2014

(86) PCT No.: PCT/JP2014/070470
§ 371 (c)(1),
(2) Date: Jan. 5, 2016

(87) PCT Pub. No.: WO2015/022868
PCT Pub. Date: Feb. 19, 2015

(65) Prior Publication Data
US 2016/0154256 A1 Jun. 2, 2016

(30) Foreign Application Priority Data
Aug. 13, 2013 (JP) ................................. 2013-168260

(51) Int. Cl.
*G02C 11/00* (2006.01)
*G02C 7/04* (2006.01)
(Continued)

(52) U.S. Cl.
CPC ............ *G02C 11/10* (2013.01); *A61B 5/1468* (2013.01); *A61B 5/14532* (2013.01); *A61B 5/6821* (2013.01); *G02C 7/04* (2013.01)

(58) Field of Classification Search
None
See application file for complete search history.

(56) References Cited

U.S. PATENT DOCUMENTS

| 2002/0049389 A1* | 4/2002 | Abreu | A61B 3/1241 600/558 |
| 2008/0044721 A1* | 2/2008 | Heller | C12Q 1/26 429/2 |
| 2011/0084834 A1 | 4/2011 | Sabeta | |

FOREIGN PATENT DOCUMENTS

EP 1941829 A2 7/2008

OTHER PUBLICATIONS

Faulk et al., Biofuel cell as a power source for electronic contact lenses, May 4, 2012, Biosensors and bioelectronics, 37, p. 38-45.*
(Continued)

*Primary Examiner* — Michael R Bloch
(74) *Attorney, Agent, or Firm* — Chip Law Group

(57) ABSTRACT

The present technology relates to a wearable device and an electricity supply system that make it possible to reduce the stress on a user in relation to electricity supply. A power generating unit is provided on the external world-side surface or the eyeball-side surface of a contact lens-type wearable device. The power generating unit generates electric power by chemical reaction with a substance contained in a secretion or a body fluid of a user wearing the wearable device, and a power managing unit supplies the electric power obtained in the power generating unit to each part of the wearable device. Thus, the power generating unit performs electricity generation using the secretion or the body fluid of the user as fuel; thereby, electric power can be stably supplied, and the stress on the user in relation to electricity supply can be reduced. The present technology can be applied to a contact lens-type wearable device.

8 Claims, 11 Drawing Sheets

(51) Int. Cl.
*A61B 5/1468* (2006.01)
*A61B 5/145* (2006.01)
*A61B 5/00* (2006.01)

(56) References Cited

OTHER PUBLICATIONS

Extended European Search Report of EP Patent Application No. 14836846.7, dated Jan. 31, 2017, 10 pages.
Falk, et al., "Miniature Biofuel Cell as a Potential Power Source for Glucose-Sensing Contact Lenses", Analytical Chemistry, American Chemical Society, vol. 85, 2013, pp. 6342-6348.
Falk, et al., "Biofuel cell as a power source for electronic contact lenses", Biosensors and Bioelectronics, Elsevier BV, vol. 37, 2012, pp. 38-45.

* cited by examiner

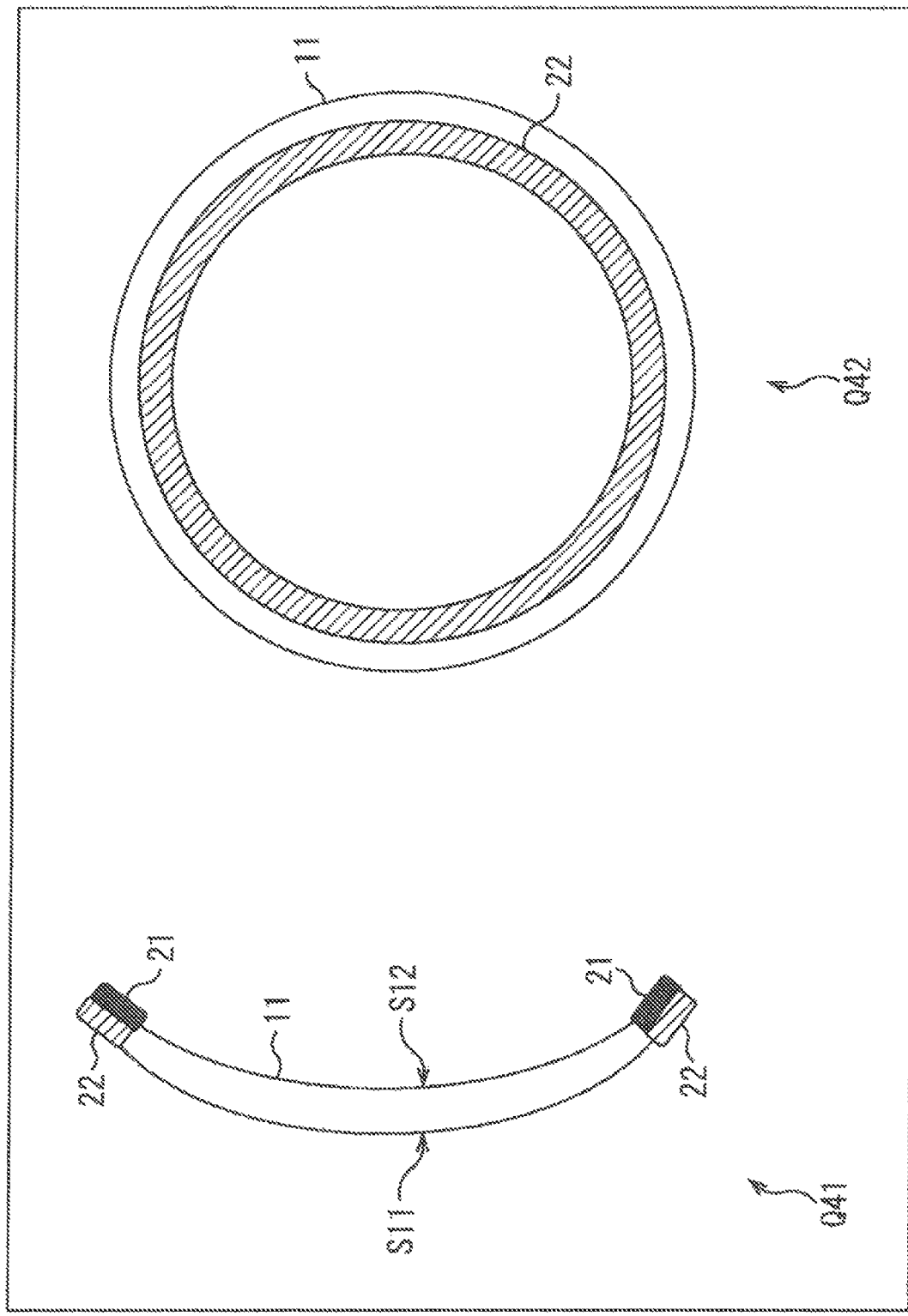

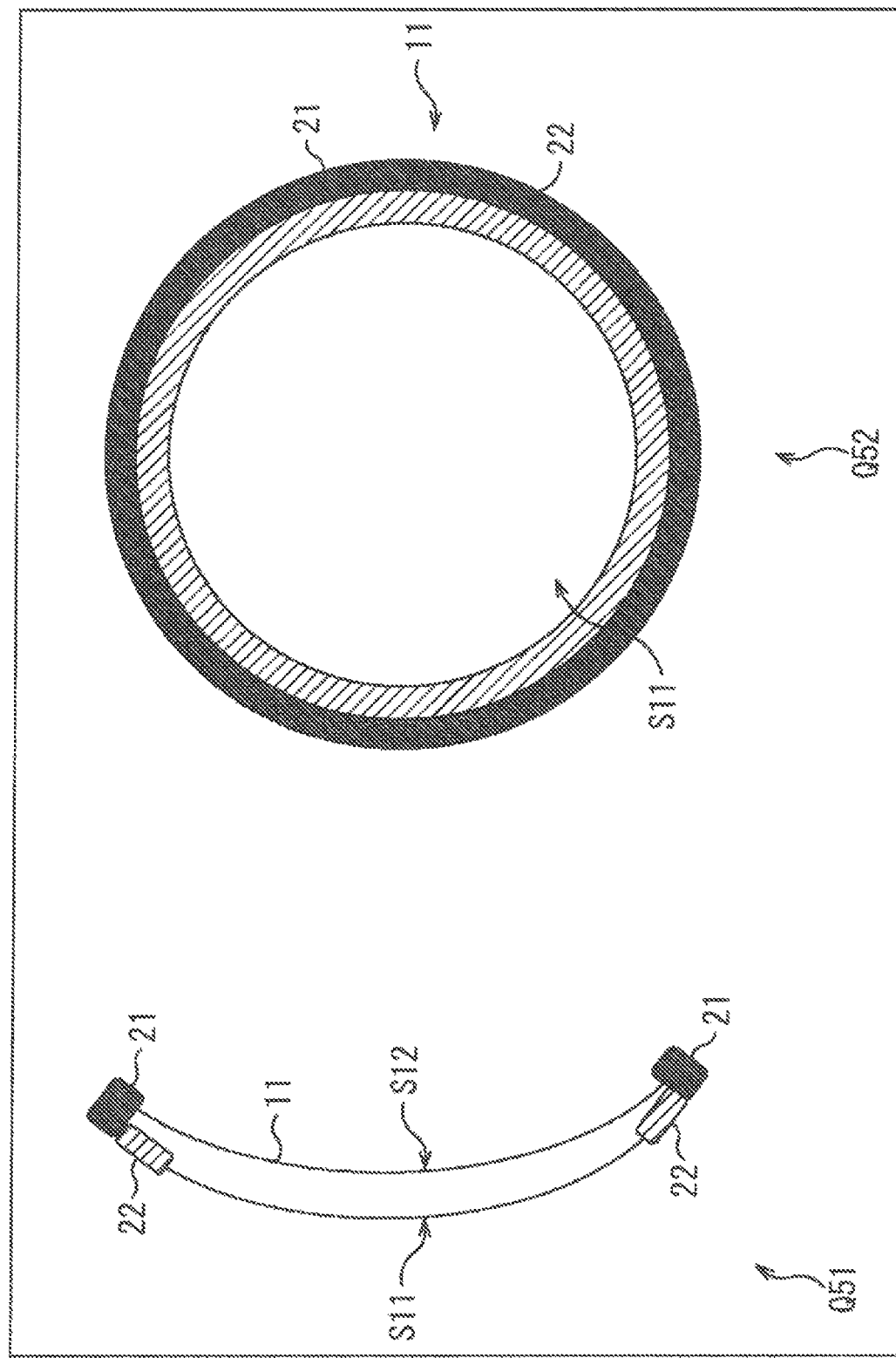

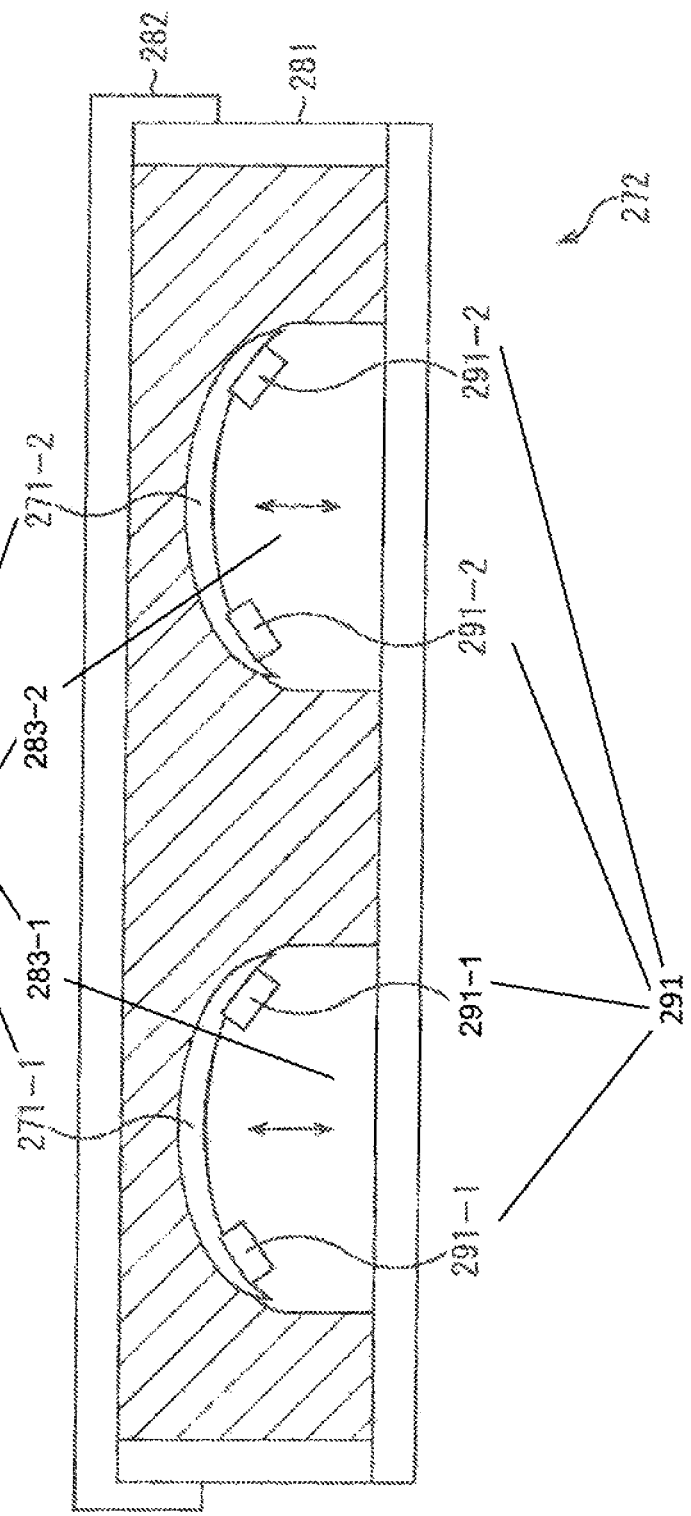

WEARABLE DEVICE AND ELECTRICITY SUPPLY SYSTEM

TECHNICAL FIELD

The present technology relates to a wearable device and an electricity supply system, and relates particularly to a wearable device and an electricity supply system that can reduce the stress on a user in relation to electricity supply.

BACKGROUND ART

Conventionally a contact lens-type display device is proposed as a wearable device that is wearable on an eye of a user (e.g. see Patent Literature 1). Since the display device is worn on an eyeball of the user and is used wirelessly, the user can make movements such as freely walking around in a state of wearing the display device.

There are also a head mount display, an eyeglass-type display, etc. as wearable devices that are worn around the eye, such as on the head of a user.

In these wearable devices, electricity supply to each part is performed by a battery provided in the wearable device.

CITATION LIST

Patent Literature

Patent Literature 1: JP 4752309B

SUMMARY OF INVENTION

Technical Problem

It is preferable for the wearable devices described above to be small in size and allow wireless use from the viewpoint of wearability.

However, in a small-sized wearable device, since there are limitations on the battery capacity that can be incorporated, the continuous driving time is generally short. Consequently, the user needs to frequently perform the charging of the wearable device, and such frequent charging actions, that is, electricity supply actions on the wearable device cause stress when the user uses the wearable device.

The present technology is developed in view of such circumstances, and makes it possible to reduce the stress on a user in relation to electricity supply.

Solution to Problem

According to a first aspect of the present technology, there is provided a wearable device wearable on an eyeball, including: a power generating unit configured to generate electric power by chemical reaction with a substance supplied from an outside; and a power managing unit configured to supply electric power obtained in the power generating unit to each part.

The power generating unit can generate electric power by chemical reaction with the substance contained in a secretion or a body fluid of a user wearing the wearable device.

The substance can be a sugar.

The wearable device can further include an electricity storage unit configured to store electric power obtained in the power generating unit.

The power generating unit can be provided on a surface on an opposite side to the eyeball side of the wearable device and generate electric power by chemical reaction with the substance contained in a tear as the secretion.

The power generating unit can be provided on a film attachable to and detachable from the wearable device.

The power generating unit can be located on a front surface of an eyelid of the user, a back surface of an eyelid of the user, or a surface of a tissue around an eye of the user when the wearable device is worn on the user.

The power generating unit can be attachable to and detachable from the wearable device.

The power generating unit can generate electric power by chemical reaction with the substance contained in at least one of blood and aqueous humor as the body fluid.

The power generating unit can be provided so as to cover an outer periphery of the wearable device.

The wearable device can further include a processing unit configured to perform processing in accordance with a concentration of the substance supplied to the power generating unit.

The wearable device can further include a processing unit configured to monitor a change in the substance contained in the secretion or the body fluid of the user supplied to the power generating unit The processing unit can estimate health condition or stress condition of the user on the basis of a monitoring result of a change in the substance.

In the first aspect of the present technology, in a wearable device wearable on an eyeball, electric power is generated in a power generating unit by chemical reaction with a substance supplied from the outside, and the electric power obtained in the power generating unit is supplied to each part.

According to a second aspect of the present technology, there is provided an electricity supply system including: a wearable device wearable on an eyeball; and a storage case configured to store the wearable device, the wearable device including a power generating unit configured to generate electric power by chemical reaction with a substance supplied from an outside, a power managing unit configured to supply electric power obtained in the power generating unit to each part, and an electricity storage unit configured to store electric power obtained in the power generating unit. The storage case is capable of retaining a storage liquid containing the substance in such a manner that the wearable device is in a state of being impregnated with the storage liquid.

In the second aspect of the present technology, in an electricity supply system composed of a wearable device wearable on an eyeball and a storage case that stores the wearable device, the wearable device is stored in the storage case in a state of being impregnated with a storage liquid, and electric power is generated in the wearable device by chemical reaction with a substance contained in the storage liquid and the obtained electric power is supplied to each part and is stored.

Advantageous Effects of Invention

According to the first aspect and the second aspect of the present technology, the stress on a user in relation to electricity supply can be reduced.

BRIEF DESCRIPTION OF DRAWINGS

FIG. 9 is a diagram showing another configuration example of the wearable device.

FIG. 10 is a diagram showing another configuration example of the wearable device.

FIG. 11 is a diagram showing a configuration example of an electricity supply system.

DESCRIPTION OF EMBODIMENTS

Figure 1:
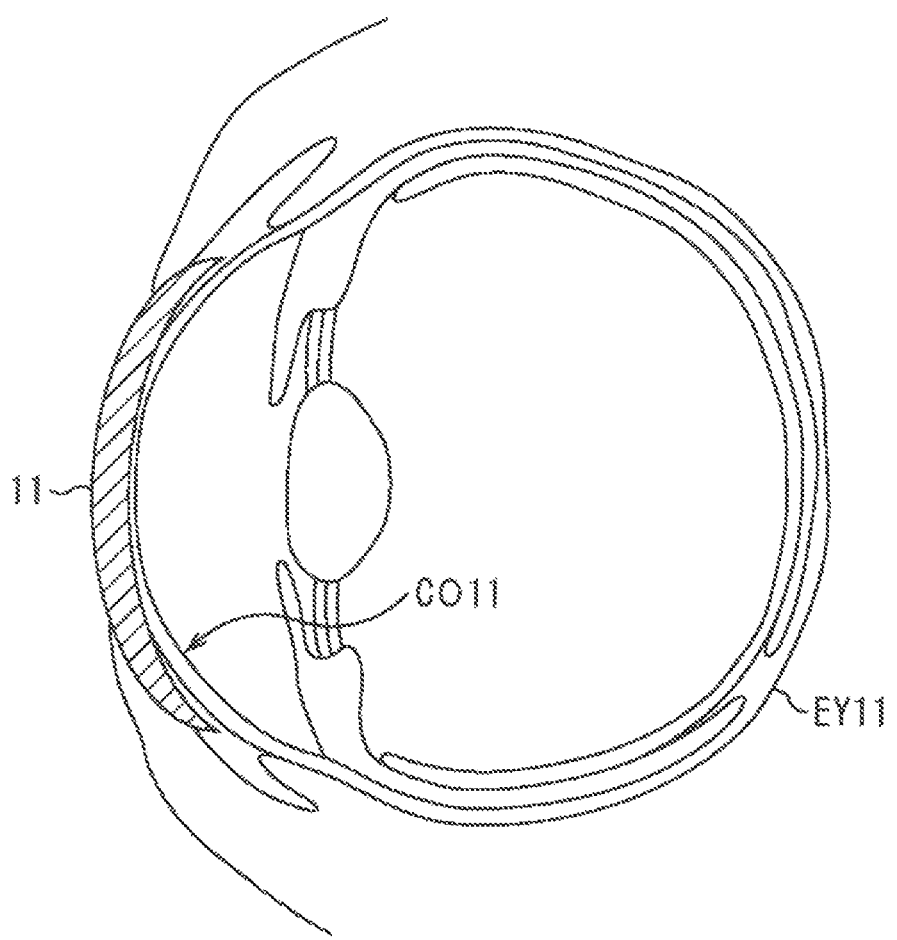
FIG. 1 is a diagram showing a wear state of a wearable device.

Hereinbelow, embodiments to which the present technology is applied are described with reference to the drawings.

(Overview of the Present Technology)

First, an overview of the present technology is described.

In the following, a description is given using as an example the case where the present technology is applied to a contact lens-type wearable device.

The present technology enables a contact lens-type wearable device to be made a small-sized, thin structure. That is, according to the present technology, in a wearable device, a configuration in which it is not necessary to provide any one or all of an electricity storage element, a charging circuit, and a terminal, coil, and antenna for performing electric power transfer and reception in a wired or wireless manner during charging can be obtained, or these elements can be downsized.

Furthermore, according to the present technology, the stress that electricity supply actions on the wearable device impose on a user can be reduced. Specifically, the number of times of charging actions (electricity supply actions) is reduced, and stress reduction is achieved by an electricity supply system with a good user interface.

Here, the electricity supply system with a good user interface is a system in which, for example, electricity supply is performed on a contact lens-type wearable device by utilizing tears etc. of a user and electricity supply is thereby performed naturally without the user's consciousness, or the like. Furthermore, electricity supply without causing a user to feel stress can be achieved also by performing electricity supply by performing eyedropping on a contact lens-type wearable device, or by electricity supply being performed in a state where the wearable device is stored in a container such as a storage case, for example.

Describing in more detail, in the present technology, a contact lens-type wearable device is provided with a battery or an electricity generating element that generates a potential difference by chemical reaction with a substance supplied from the outside, for example.

The element that generates electric power to be supplied to each part of the wearable device may be one that generates electric power by generating a potential difference, or may be one that generates electric power by generating a current. In the following, elements such as a battery and an electricity generating element that generate electric power to be supplied to the wearable device may be referred to as simply a power generating unit.

In the present technology, a method in which the substance necessary for such a power generating unit to generate electricity is obtained as a biological secretion such as tears existing in the environment around the eyeball, a method in which the substance necessary for electricity generation is obtained from a body fluid such as aqueous humor or blood, or a method in which the substance necessary for electricity generation is supplied from the outside of the living body, such as by eyedropping or liquid immersion in a container, is used.

For example, in the case where the power consumption of the contact lens-type wearable device is always smaller than the electric power generated in the power generating unit, when the user simply wears the wearable device, continuous energy supply to the wearable device can be performed by a substance of the living body or the outside of the living body.

Thereby, in the wearable device, a terminal, electrode, coil, or antenna for performing charging from the outside in a wired or wireless manner, an electricity storage element and a charging circuit for storing the energy obtained by electricity generation, etc. are not necessarily needed. That is, the contact lens-type wearable device can be downsized more.

On the other hand, in the case where the power consumption in the wearable device may be larger than the generated electric power, the energy generated by electricity generation may be stored in an electricity storage element through a charging circuit, and an electric power amount in accordance with necessity may be used. Hence, in the wearable device, a terminal, electrode, coil, antenna, etc. related to electricity supply in a wired or wireless manner are not necessarily needed. Therefore, the contact lens-type wearable device can be downsized likewise.

More specifically, as the battery or the electricity generating element that generates a potential difference by chemical reaction, which is an example of the power generating unit referred to herein, a bio-battery that generates electricity by sugar-enzyme reaction or the like is given. In the case where a bio-battery is used as the power generating unit, a component that contributes to reaction related to electricity generation is a sugar, and the sugar is contained in, for example, a component of blood and tears.

As the electricity storage element that stores the electric power (energy) generated by the power generating unit, a secondary battery, a capacitor, a lithium ion capacitor, or the like may be used. When electricity storage on the electricity storage element is performed, the wearable device may be provided with a rectifying circuit, a regulator, a charging circuit, etc. as necessary.

As the position where the battery or the electricity generating element that generates a potential difference by chemical reaction is installed as the power generating unit in the contact lens-type wearable device, the following three positions are possible. That is, the power generating unit may be disposed on any one of a surface on the opposite side to the eyeball side of the wearable device (hereinafter, occasionally referred to as an external world-side surface), an eyeball-side surface of the wearable device, and a position traversing the external world-side surface and the eyeball-side surface, that is, a portion of the side surface of the wearable device. Also a configuration in which the power generating unit is disposed in the interior of the wearable device and an opening for supplying the substance necessary for electricity generation to the power generating unit is provided on the surface of the wearable device is possible, for example.

The arrangement position of the power generating unit is preferably near the outer periphery that does not come into the visual field of the user when the user wears the wearable device on the eyeball. However, when the wearable device has in its part a figure that obstructs the visual field of the user, for example like a color contact lens, the power generating unit may be disposed in the region of the figure portion.

The power generating unit provided in the wearable device may be attachable to and detachable from the wearable device. For example, a configuration in which the power generating unit is provided on a film that is attachable to and detachable from the wearable device, and the wearable device and the power generating unit are connected via an electrode is possible.

Furthermore, also a configuration in which the power generating unit is embedded in the body of the user, such as on the inside of the eyelid, only an electrode provided in the power generating unit is exposed, and the electrode and an electrode provided on the surface of the wearable device are brought into contact to perform electricity supply is possible.

In the case where a battery or an electricity generating element that generates electricity by utilizing part of a secretion such as tears or a body fluid such as blood, or a plurality of components of them is used as the power generating unit, it can be said that the electricity generation condition indicates the condition of the component of the secretion such as tears or the body fluid such as blood, which is the source of electricity generation. Furthermore, the condition of the secretion or the body fluid of the user indicates the stress condition or the health condition of the user. Therefore, from the electricity generation amount in the power generating unit, it becomes possible not only to obtain the operating power of the contact lens-type wearable device, but also to estimate the stress condition or the health condition of the user who is the wearing person.

There is also a case where it is desired to supply large electric power instantaneously, such as when it is desired to charge the electricity storage element of the wearable device quickly. In such a case, when a liquid that contributes to reaction related to electricity generation is supplied by eyedropping or liquid immersion to the battery or the electricity generating element that generates a potential difference by chemical reaction, large electric power can be obtained instantaneously by supplying a liquid with a high concentration of the component that contributes to reaction related to electricity generation.

In the case where there are restrictions on the lifetime etc. of a catalyst used for the battery or the electricity generating element that generates a potential difference by chemical reaction, when it is desired to generate electricity for a relatively long time without degrading the performance of the catalyst, a measure of supplying a liquid with a reduced concentration of the component that contributes to reaction related to electricity generation may be taken.

Moreover, in addition to the supply to the power generating unit of a liquid that contributes to reaction related to electricity generation, it is also possible to supply to the power generating unit a reducing agent that restores the degraded catalyst function, and to supply a pH adjuster, a neutralizer, etc. against an acid etc. that are produced in the reaction related to electricity generation and may adversely influence the human body.

(First Embodiment)
(Configuration Example of the Wearable Device)

Next, a specific embodiment of the present technology described above is described.

The wearable device to which the present technology is applied is worn on an eyeball EY11 of a user as shown in FIG. 1, for example. This example is in a state where a contact lens-type wearable device 11 is worn on the eyeball EY11 so as to cover the entire cornea CO11.

The wearable device 11 is in a shape that can be put on and taken off the eyeball EY11 of the user, like what is called a contact lens.

Figure 2:
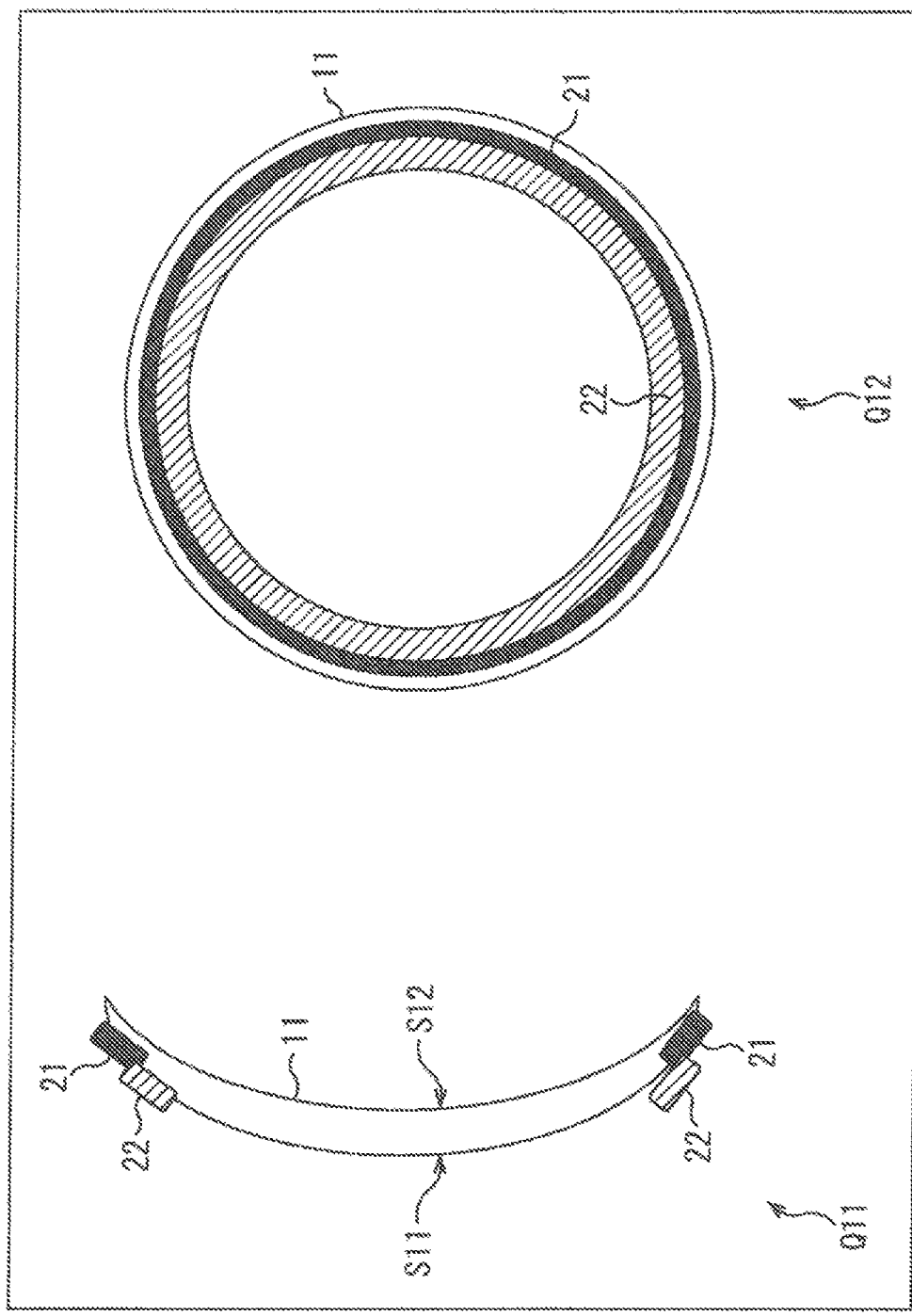
FIG. 2 is a diagram showing a configuration example of the wearable device.

The wearable device 11 is provided with a power generating unit 21 and an electricity storage element 22 as shown in FIG. 2.

In FIG. 2, the drawing of the wearable device 11 shown by arrow Q11 shows a cross-sectional view when the wearable device 11 is viewed from the side surface side.

In this example, in the drawing of the wearable device 11, the surface on the left side is an external world-side surface S11 that is located on the opposite side to the eyeball side when the user wears the wearable device 11, and a surface S12 facing the eyeball side is an eyeball-side surface.

On the external world-side surface S11 of the wearable device 11, the power generating unit 21 is provided along the outer periphery of the wearable device 11, and the electricity storage element 22 is provided along the power generating unit 21 on the inside of the power generating unit 21, that is, on the center side of the surface S11.

When the wearable device 11 shown by arrow Q11 is viewed in the direction from the left side to the right side in the drawing, as shown by arrow Q12, the power generating unit 21 and the electricity storage element 22 are provided in an end portion of the wearable device 11. The drawing shown by arrow Q12 shows a view when the wearable device 11 is viewed from the same direction as when the user wearing the wearable device 11 is viewed from the front side, that is, a front view of the wearable device 11.

In the wearable device 11 shown by arrow Q12, the power generating unit 21 and the electricity storage unit 22 are provided along the end (outer periphery) of the wearable device 11; and these elements are located outside the visual field of the user wearing the wearable device 11, or are located such that the influence on the visual field is in a range acceptable to the user. The power generating unit 21 and the electricity storage element 22 may be disposed in any positional relationship. For example, the power generating unit 21 may be disposed on the inside of the electricity storage element 22 provided along the end of the wearable device 11, or the power generating unit 21 and the electricity storage element 22 may be disposed on one circle in an arbitrary pattern.

The power generating unit 21 is formed of, for example, a bio-battery that generates a potential difference by chemical reaction with a substance supplied from the outside to the external world-side surface S11 of the wearable device 11.

In a state where the wearable device 11 is worn on the eyeball of the user, the power generating unit 21 generates electricity using a sugar component contained in tears secreted from the user, for example. That is, the sugar component of the tear is utilized as fuel for the bio-battery as the power generating unit 21.

Upon being supplied with a tear, the power generating unit 21 generates electric power by chemical reaction with a sugar component contained in the tear. The generated electric power is supplied to each part of the wearable device 11, and is supplied to and stored in the electricity storage element 22, as appropriate.

In particular, since tears tend to collect near the portion where the eyeball and the eyelid are in contact, tears can be supplied to the power generating unit 21 more stably by providing the power generating unit 21 in an outer peripheral portion of the wearable device 11, that is, in a portion in contact with the eyelid of the wearable device 11.

In a state where the wearable device 11 is worn on the user, since electric power is supplied at all times from the power generating unit 21 by the tear every time the user blinks, electric power is stably supplied to each part of the wearable device 11. That is, when the wearable device 11 performs its function in the range of the generated electric power, the electricity storage element 22 may not necessarily be provided in the wearable device 11.

However, the sugar component contained in the tear is thin as compared to the sugar component contained in blood, and the generated electric power is small. Hence, the wearable device 11 is configured to be capable of continuously performing operation of very low power consumption and sleep operation.

When the wearable device 11 is configured to be capable of performing operation of low power consumption and sleep operation, it is not necessarily needed to store electricity in the electricity storage element 22.

Thus, by the wearable device 11, when the user wears the wearable device 11, electric power can be generated by the tear secreted from the eye of the user, and electric power can be supplied to each part as necessary and electricity can be stored.

Therefore, electric power can be obtained without causing the user to be conscious of electricity supply to the wearable device 11, and the stress on the user in relation to electricity supply can be reduced. In addition, since electric power can be stably obtained by the tear, the user does not need to perform charging actions (electricity supply actions) oneself.

Although an example in which the power generating unit 21 is provided on the external world-side surface S11 of the wearable device 11 is described in FIG. 2, the power generating unit 21 may be provided in the interior of the wearable device 11, for example. In such a case, an opening for supplying tears to the power generating unit 21 may be provided on at least one of the external world-side surface S11 and the eyeball-side surface S12 of the wearable device 11. The opening may be provided with a function such as controlling liquid supply etc., for example by providing a pump function by using capillary force, etc.

In the case where larger power consumption is needed for the contact lens-type wearable device 11, when the wearable device 11 is driven intermittently, a method in which electric power is stored in the electricity storage element 22 and the electric power stored in the electricity storage element 22 is used as necessary is possible. However, in such a case, electric power is not necessarily always stored as much as needed, and there is a case where it is not possible to perform all the functions desired to be used.

In such a case, an eyedrop liquid with a higher concentration of the sugar than the tear may be dropped onto the user; thus, larger electric power can be generated in the power generating unit 21, and the wearable device 11 can be made to perform highly functional operations.

When the enzyme of the bio-battery as the power generating unit 21 has deteriorated, the enzyme of the bio-battery may be loaded by eyedropping or by taking off the wearable device 11 itself, or the wearable device 11 itself may be exchanged for a new one.

In the wearable device 11, the change in a component of the tear may be monitored from the electric power obtained by the component of the tear secreted from the eye of the user. In such a case, for example, a line for monitoring with a high impedance for reading the change in the component of the tear is provided in the wearable device 11. A numerical value such as the concentration of the sugar found from the electric power value that is converted to a digital value by an analog/digital (A/D) conversion unit connected to the line for monitoring is recorded in the recording area.

(Functional Configuration Example of the Wearable Device)

Figure 3:
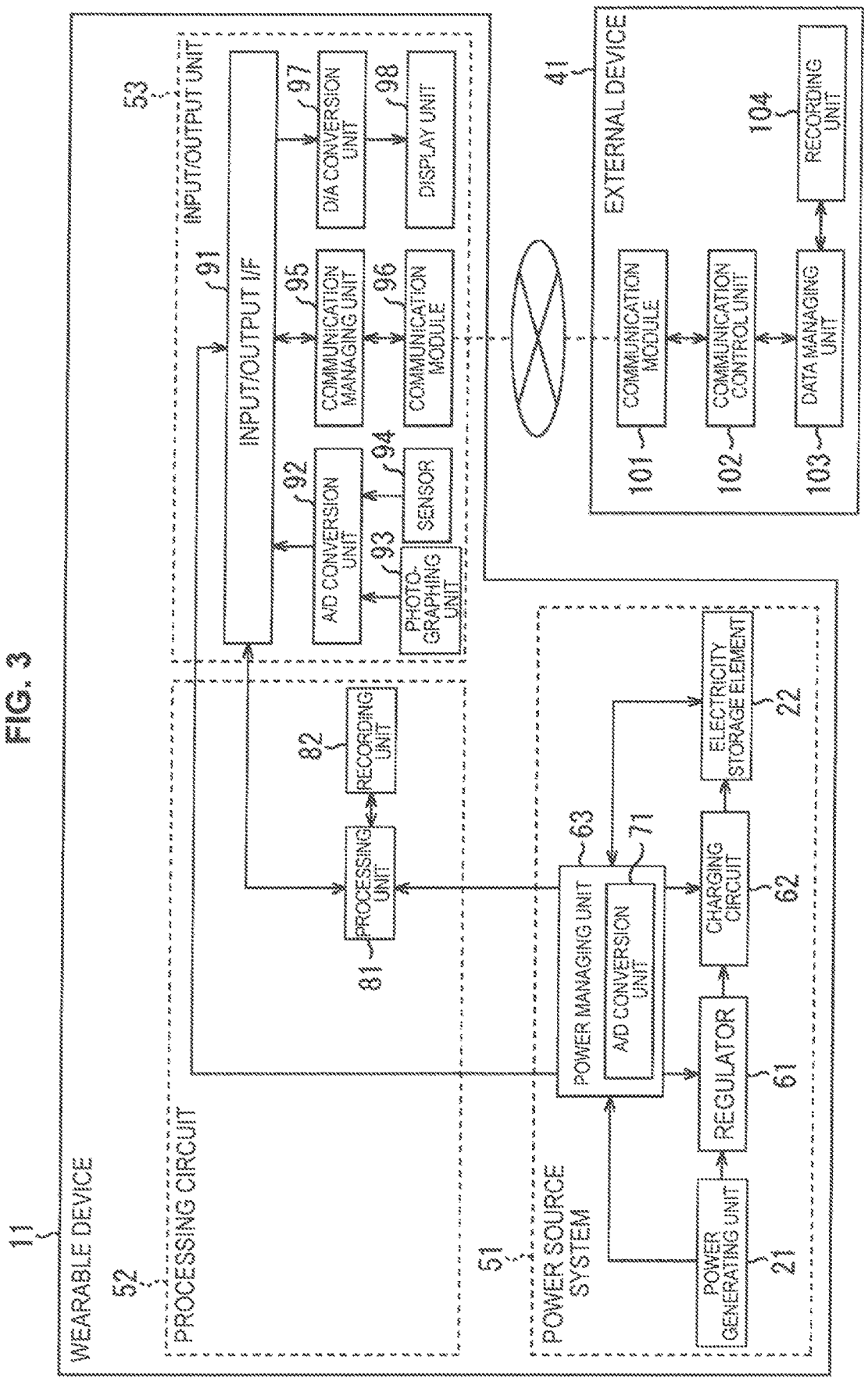
FIG. 3 is a diagram showing a configuration example of functions of the wearable device.

The wearable device 11 described above is, in more detail, configured in a manner shown in FIG. 3, for example. FIG. 3 shows a functional configuration example of the wearable device 11. In FIG. 3, portions corresponding to those in FIG. 2 are marked with the same reference numerals, and a description thereof is omitted as appropriate.

In this example, the wearable device 11 is connected to an external device 41 by wired or wireless communication, and performs the transfer and reception of information with the external device 41 as necessary.

The wearable device 11 is composed of a power source system 51, a processing circuit 52, and an input/output unit 53.

The power source system 51 performs electricity generation, and supplies the electric power obtained by electricity generation to the processing circuit 52 and the input/output unit 53. The processing circuit 52 is supplied with electric power from the power source system 51, and performs various processings on the basis of the information etc. supplied from the input/output unit 53. The processing circuit 52 supplies various pieces of information to the input/output unit 53 as necessary The input/output unit 53 is supplied with electric power from the power source system 51, and supplies the inputted information to the processing circuit 52 and outputs the information supplied from the processing circuit 52.

In the power source system 51, the power generating unit 21, a regulator 61, a charging circuit 62, the electricity storage element 22, and a power managing unit 63 are provided.

The regulator 61 performs voltage step-up or voltage step-down on the electric power generated in the power generating unit 21, and supplies the resulting electric power to the charging circuit 62. The charging circuit 62 supplies the electric power supplied from the regulator 61, in more detail the charge obtained by electricity generation, to the electricity storage element 22 to cause the charge to be stored.

The power managing unit 63 controls each part of the power source system 51.

For example, the power managing unit 63 monitors the electricity generation amount in the power generating unit 21 and the electric power amount stored in the electricity storage element 22, and performs switching to operation of low power consumption or sleep operation as necessary to set the regulator 61 and the charging circuit 62 to the sleep state. The power managing unit 63 supplies the electric power obtained in the power generating unit 21 or the electric power stored in the electricity storage element 22 to the processing circuit 52 and the input/output unit 53.

The power managing unit 63 includes an A/D conversion unit 71. The A/D conversion unit 71 is connected to the power generating unit 21 by a line for monitoring with a high impedance; and converts the electricity generation amount in the power generating unit 21 to a digital value, and supplies the vale to the processing circuit 52.

The processing circuit 52 includes a processing unit 81 and a recording unit 82.

The processing unit 81 is supplied with electric power from the power managing unit 63, and performs various processings using the information supplied from the power managing unit 63 or the input/output unit 53 as appropriate.

For example, the processing unit 81 finds the concentration of the sugar component contained in the tear of the user from the value indicating the electricity generation amount supplied from the A/D conversion unit 71, and supplies the resulting value of the concentration to the recording unit 82 to cause the value to be recorded. Since the electromotive force in the power generating unit 21 is determined by the concentration of the sugar component, the concentration of the sugar component can be detected on the basis of the electromotive force.

Furthermore, for example, the processing unit 81 estimates the health condition, feeling, or stress condition of the user on the basis of the concentration value of the sugar component recorded in the recording unit 82, and supplies the estimation result to the input/output unit 53. Thus, the processing unit 81 monitors the change in the electricity generation amount supplied from the A/D conversion unit 71, that is, the change in concentration of the sugar component contained in the tear, and estimates the health condition or stress condition of the user on the basis of the monitoring result.

The processing circuit 52 etc. may be provided with an element that detects the concentration of each component of the tear, such as sodium, from the tear supplied to the wearable device 11, and the processing unit 81 may estimate the health condition, feeling, stress condition, etc. of the user on the basis of the detection result of the element.

The recording unit 82 records information such as the concentration value of the sugar component supplied from the processing unit 81, and supplies the recorded information to the processing unit 81.

The input/output unit 53 is composed of an input/output interface (I/F) 91, an A/D conversion unit 92, a photographing unit 93, a sensor 94, a communication managing unit 95, a communication module 96, a digital/analog (D/A) conversion unit 97, and a display unit 98.

The input/output I/F 91 operates by being supplied with electric power from the power managing unit 63, and supplies electric power to each part of the input/output unit 53. The input/output I/F 91 supplies the information supplied from the A/D conversion unit 92 and the communication managing unit 95 to the processing unit 81, and supplies the information supplied from the processing unit 81 to the communication managing unit 95 and the D/A conversion unit 97.

The A/D conversion unit 92 converts the image data supplied from the photographing unit 93 and the information supplied from the sensor 94 from analog data to digital data, and supplies the digital data to the input/output I/F 91.

The photographing unit 93 photographs the external world side of the user, that is, photographs an image from the visual point of the user in a state where the user wears the wearable device 11, and supplies the obtained image data to the A/D conversion unit 92, for example. The image photographed in the photographing unit 93 is supplied to the processing unit 81 and is recorded in the recording unit 82; or is processed in the processing unit 81 and is supplied to the display unit 98 to be displayed on the display unit 98 as appropriate, for example.

The sensor 94 detects the movement of the user wearing the wearable device 11, and supplies the detection result to the A/D conversion unit 92, for example. On the basis of the movement detected in the sensor 94, the display control of the image that the processing unit 81 causes the display unit 98 to display is performed, and the input operation of the user is detected, for example.

The communication managing unit 95 controls the communication by the communication module 96. For example, the communication managing unit 95 supplies the information supplied from the processing unit 81 via the input/output I/F 91 to the communication module 96 and causes the information to be transmitted to the external device 41, and supplies the information received by the communication module 96 firm the external device 41 to the processing unit 81 via the input/output I/F 91.

The communication module 96 transmits the information supplied from the communication managing unit 95 to the external device 41 in a wireless or wired manner, and receives the information transmitted from the external device 41 and supplies the information to the communication managing unit 95.

The D/A conversion unit 97 converts the image data etc. supplied from the input/output I/F 91 from digital data to analog data, and supplies the analog data to the display unit 98.

The display unit 98 is formed of, for example, an organic light emitting diode (OLED), a liquid crystal display element, or the like, and displays an image on the basis of the image data supplied from the D/A conversion unit 97. The light outputted by the display unit 98 in order to display an image passes through the pupil of the user wearing the wearable device 11 and reaches the retina, and the image is perceived by the user, for example.

The external device 41 connected to the wearable device 11 includes a communication module 101, a communication control unit 102, a data managing unit 103, and a recording unit 104.

The communication module 101 receives the information transmitted by the communication module 96 of the wearable device 11 and supplies the information to the communication control unit 102, and transmits the information supplied from the communication control unit 102 to the wearable device 11 in a wireless or wired manner.

The communication control unit 102 controls the communication module 101; and supplies the information supplied from the communication module 101 to the data managing unit 103, and supplies the information supplied from the data managing unit 103 to the communication module 101.

The data managing unit 103 manages the information recorded in the recording unit 104. For example, the data managing unit 103 supplies the information supplied from the communication control unit 102 etc. to the recording unit 104 to cause the information to be recorded, and reads information from the recording unit 104 and supplies the information to the communication control unit 102 etc. The recording unit 104 records the information obtained from the data managing unit 103 in accordance with the control of the data managing unit 103, and supplies the recorded information to the data managing unit 103.

Although the case where the wearable device 11 communicates with the external device 41 to transfer and receive information is described in the example shown in FIG. 3, the wearable device 11 may not communicate with the external device 41.

The configuration of the wearable device 11 is not limited to the configuration shown in FIG. 3; for example, the electricity storage element 22, the regulator 61 to the power managing unit 63, the A/D conversion unit 92 to the display unit 98, etc. may be provided in accordance with necessity. That is, configurations not including part or all of these elements are possible.

(Modification Example 1 of the First Embodiment)
(Functional Configuration Example of the Wearable Device)

In the above, it is described that a liquid for electricity generation may be supplied to the wearable device 11 by eyedropping. In addition, it is known that the sugar concentration and the electromotive force of the bio-battery correlate.

Thus, for example, the wearable device 11 may perform different operations in accordance with the sugar concentration in the eyedrop liquid supplied to the bio-battery as the power generating unit 21.

Figure 4:
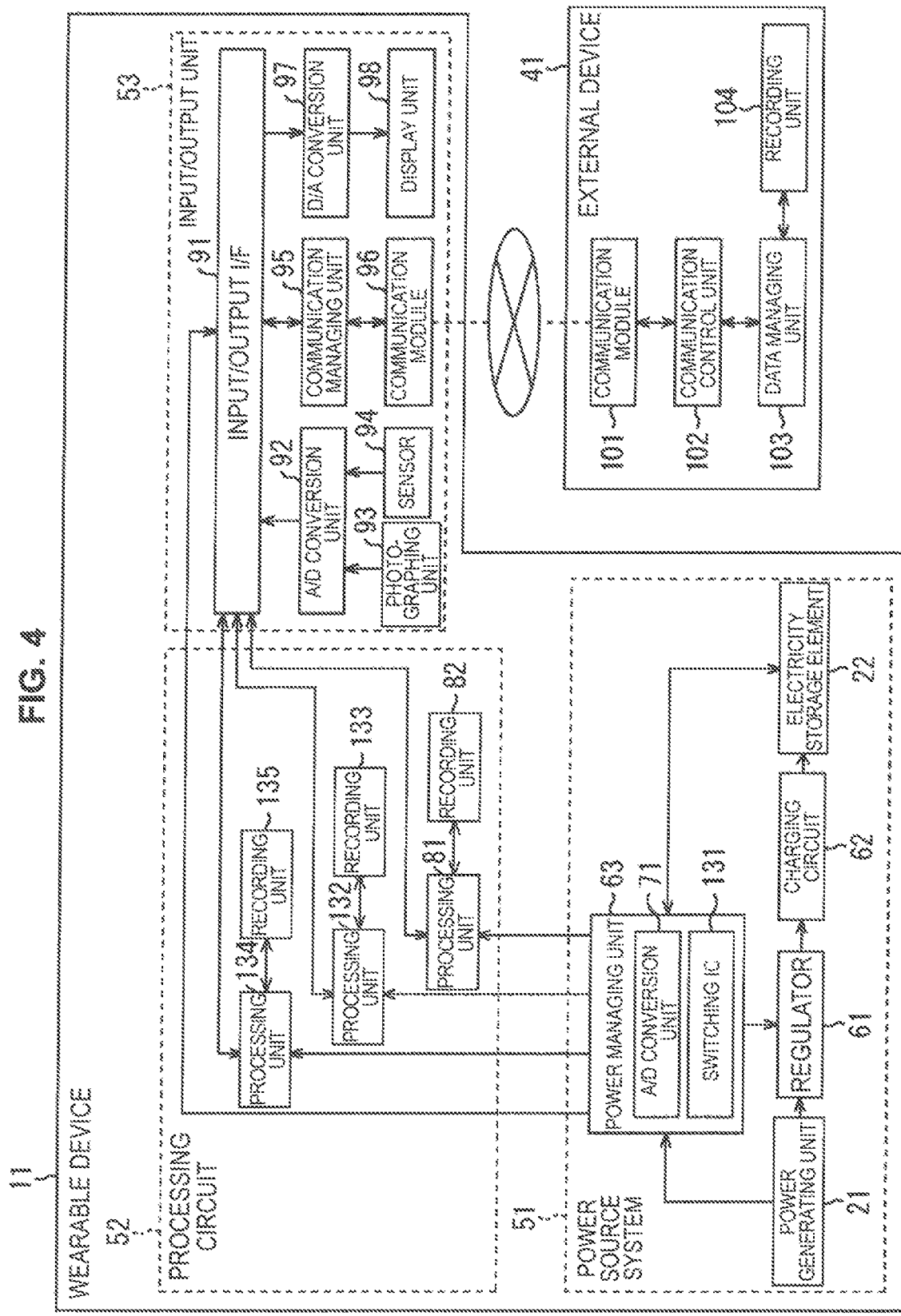
FIG. 4 is a diagram showing a configuration example of other functions of the wearable device.

In such a case, the wearable device 11 is configured in a manner shown in FIG. 4, for example. In FIG. 4, portions corresponding to those in FIG. 3 are marked with the same reference numerals, and a description thereof is omitted as appropriate.

The wearable device 11 shown in FIG. 4 differs from the wearable device 1 shown in FIG. 3 in that a switching IC 131, a processing unit 132, a recording unit 133, a processing unit 134, and a recording unit 135 are further provided; otherwise, the configuration is the same.

The switching IC 131 is provided in the power managing unit 63; and monitors the input voltage supplied from the power generating unit 21, and switches the circuit that is electrically connected to the power managing unit 63 in accordance with the input voltage. That is, the switching IC 131 causes the power managing unit 63 to be connected to any one or a plurality of combinations of the processing unit 81, the processing unit 132, and the processing unit 134, in accordance with the electromotive force in the power generating unit 21 determined by the concentration of the sugar component supplied.

The processing unit 132 is supplied with electric power from the power managing unit 63, and performs various processings using the information supplied from the power managing unit 63 or the input/output I/F 91.

For example, the processing unit 132 finds the concentration of the sugar component contained in the tear of the user from the value indicating the electricity generation amount supplied from the power managing unit 63, supplies the value of the concentration to the recording unit 133 to cause the value to be recorded, and reads the information recorded in the recording unit 133 and supplies the information to the input/output I/F 91.

The processing unit 134 is supplied with electric power from the power managing unit 63, and performs various processings using the information supplied from the power managing unit 63 or the input/output I/F 91.

For example, the processing unit 134 finds the concentration of the sugar component contained in the tear of the user from the value indicating the electricity generation amount supplied from the power managing unit 63, supplies the value of the concentration to the recording unit 133 to cause the value to be recorded, and reads the information recorded in the recording unit 135 and supplies the information to the input/output I/F 91.

Thus, in accordance with the switching of the supply destination of the information outputted from the power managing unit 63 which is performed by the switching IC 131, any one of the processing unit 81, the processing unit 132, and the processing unit 134 performs processing on the basis of the information supplied from the power managing unit 63. The processings performed by the processing unit 81, the processing unit 132, and the processing unit 134 may be the same, or may be different processings.

(Second Embodiment)
(Configuration Example of the Wearable Device)

Although an example in which the power generating unit 21 and the electricity storage element 22 are provided on the external world-side surface of the wearable device 11 is described in the above, the power generating unit 21 and the electricity storage unit 22 may be attachable to and detachable from the wearable device.

Figure 5:
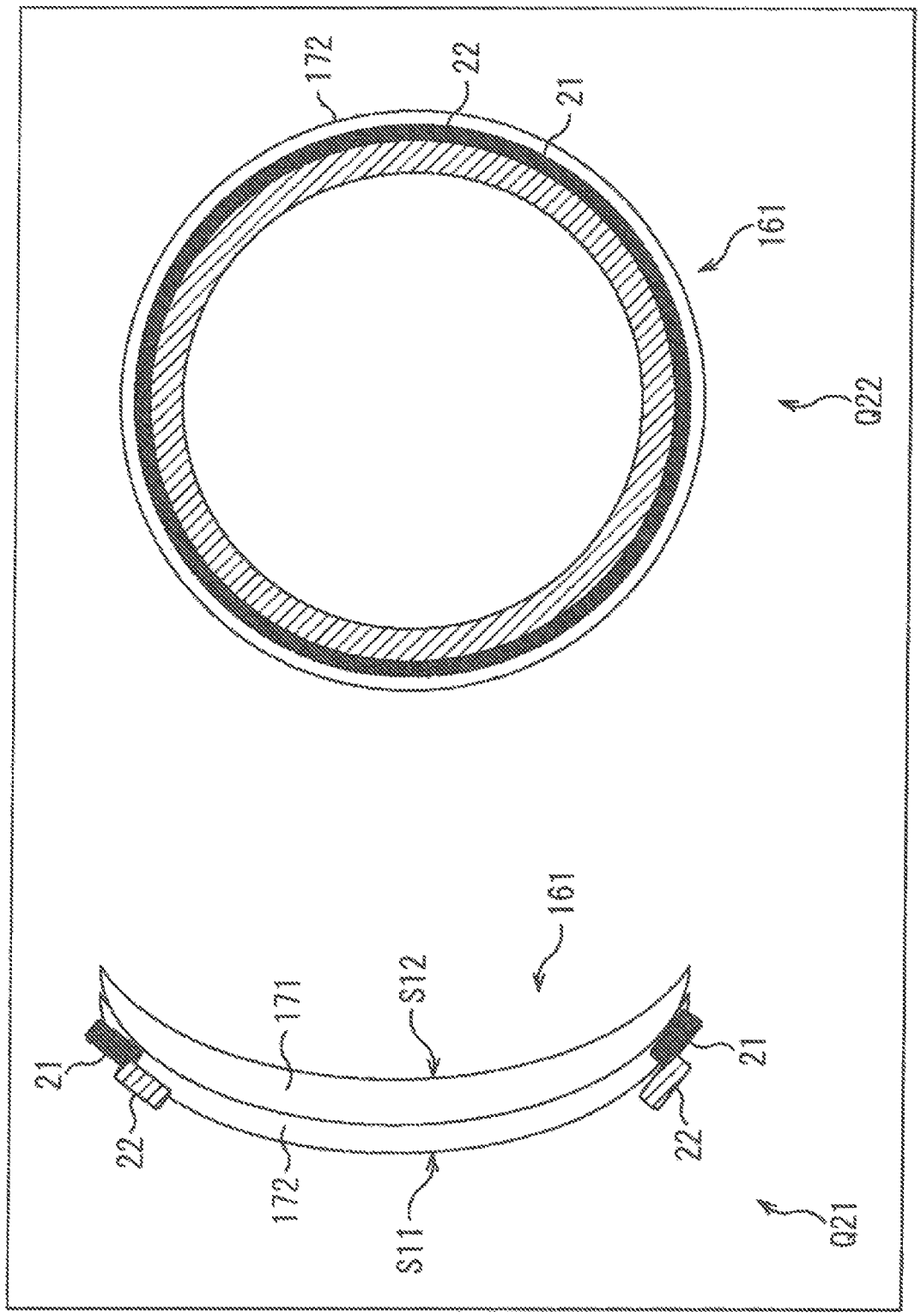
FIG. 5 is a diagram showing another configuration example of the wearable device.

In such a case, the wearable device is configured in a manner shown in FIG. 5, for example. In FIG. 5, portions corresponding to those in FIG. 2 are marked with the same reference numerals, and a description thereof is omitted as appropriate.

In FIG. 5, the drawing of a wearable device 161 shown by arrow Q21 shows a cross-sectional view when the wearable device 161 is viewed from the side surface side.

In this example, in the drawing of the wearable device 161, the surface on the left side is the external world-side surface S11 that is located on the opposite side to the eyeball side when the user wears the wearable device 161, and the surface S12 facing the eyeball side is the eyeball-side surface.

The wearable device 161 is in a shape that can be put on and taken off the eyeball of the user, similarly to the wearable device 11 described with reference to FIG. 1.

The wearable device 161 is composed of a main body 171 that is to be worn on the eyeball of the user and an exchangeable film 172 that is attachable to and detachable from the external world-side surface of the main body 171. This example is in a state where the film 172 is attached to the external world-side surface of the main body 171 so as to cover the main body 171.

The power generating unit 21 is provided on the external world-side surface S11 of the film 172 along the outer periphery of the film 172, and the electricity storage element 22 is provided on the inside of the power generating unit 21 along the power generating unit 21.

When the wearable device 161 shown by arrow Q21 is viewed in the direction from the left side to the right side in the drawing, as shown by arrow Q22, the power generating unit 21 and the electricity storage element 22 are provided in an end portion of the film 172 forming the wearable device 161. The drawing shown by arrow Q22 shows a view when the wearable device 161 is viewed from the same direction as when the user wearing the wearable device 161 is viewed from the front side, that is, a front view of the wearable device 161.

In the wearable device 161 shown by arrow Q22, the power generating unit 21 and the electricity storage element 22 are provided along the end (outer periphery) of the film 172; and these elements are located outside the visual field of the user wearing the wearable device 161, or are located such that the influence on the visual field is in a range acceptable to the user.

The main body 171 is configured to include the processing circuit 52 and the input/output unit 53 shown in FIG. 3, and the film 172 is configured to include the power source system 51 shown in FIG. 3, for example. In a state where the main body 171 and the film 172 are stuck together, a not-illustrated electrode provided on the surface of the main body 171 and a not-illustrated electrode provided near the power generating unit 21 on the surface of the film 172 are in a state of being in contact, and electric power is supplied from the film 172 to the main body 171 via these electrodes.

Thus, in the contact lens-type wearable device 161, the main body 171 and the film 172 provided with the power generating unit 21 formed of a bio-battery or the like are formed separately. Thereby, even when, for example, the electricity generation performance of the film 172 provided with the power generating unit 21 has become weak or the like, the main body 171 of the same wearable device 161 can be used continuously by exchanging the film 172.

Also in the wearable device 161, in a state where the wearable device 161 is worn on the eyeball of the user, the power generating unit 21 generates electricity using a sugar component contained in the tear secreted from the user in ordinary times. That is, the sugar component of the tear is utilized as fuel for the bio-battery as the power generating unit 21.

In a state where the wearable device 161 is worn on the user, since electric power is supplied at all times from the power generating unit 21 by the tear every time the user blinks, electric power is stably supplied to each part of the wearable device 161. That is, when the wearable device 161 performs its function in the range of the generated electric power, the electricity storage element 22 may not necessarily be provided in the wearable device 161.

However, the sugar component contained in the tear is thin as compared to the sugar component contained in blood, and the generated electric power is small. Hence, the wearable device 161 is configured to be capable of continuously performing operation of very low power consumption and sleep operation. When the wearable device 161 is thus configured, it is not necessarily needed to store electricity in the electricity storage element 22.

Thus, by the wearable device 161, electric power can be generated by the tear secreted from the eye of the user, and electric power can be supplied to each part as necessary and electricity can be stored. Therefore, electric power can be obtained without causing the user to be conscious of electricity supply to the wearable device 161, and the stress on the user in relation to electricity supply can be reduced. In addition, since electric power can be stably obtained by the tear, the user does not need to perform charging actions oneself.

In the case where larger power consumption is needed for the contact lens-type wearable device 161, when the wearable device 161 is driven intermittently, a method in which electric power is stored in the electricity storage element 22 and the electric power stored in the electricity storage element 22 is used as necessary is possible. However, in such a case, electric power is not necessarily always stored as much as needed, and there is a case where it is not possible to perform all the functions desired to be used.

In such a case, an eyedrop liquid with a higher concentration of the sugar than the tear may be dropped onto the user; thus, larger electric power can be generated in the power generating unit 21, and the wearable device 161 can be made to perform highly functional operations.

Furthermore, for example, since the sugar concentration and the electromotive force of the bio-battery as the power generating unit 21 correlate, the wearable device 161 may be made to perform different operations in accordance with the concentration of the sugar in the eyedrop liquid supplied to the bio-battery as the power generating unit 21. In such a case, the functional configuration of the wearable device 161 is the same as that of the wearable device 11 shown in FIG. 4, for example.

When the enzyme of the bio-battery as the power generating unit 21 has deteriorated, the enzyme of the bio-battery may be loaded by eyedropping or by detaching the film 172 from the main body 171, or the film 172 itself may be exchanged for a new one.

In order to facilitate the detachment of the film 172 from the main body 171, the film 172 and the main body 171 may be configured to have different wettabilities, for example. That is, when the film 172 is configured to have hydrophobic properties and the main body 171 to have hydrophilic properties, it becomes easier to detach the film 172 from the main body 171.

In the wearable device 161, the change in a component of the tear may be monitored from the electric power obtained by the component of the tear secreted from the eye of the user. In such a case, similarly to the case described with reference to FIG. 3, the A/D conversion unit 71 converts the electricity generation amount in the power generating unit 21 to a digital value, and supplies the value to the processing unit 81, for example. The processing unit 81 finds the concentration of the sugar component contained in the tear of the user from the value obtained in the A/D conversion unit 71, and causes the concentration to be recorded in the recording unit 82.

(Third Embodiment)
(Configuration Example of the Wearable Device)

Also a configuration in which the external world-side surface of the contact lens-type wearable device is provided with an electrode and the power generating unit 21 attachable to and detachable from the electrode is provided is possible. In such a case, for example, the bio-battery as the power generating unit 21 is fixed onto the front surface of the eyelid, the back surface of the eyelid, or the surface of a tissue around the eye by adhesion or embedment. The surface as the power generating unit 21 is provided with an electrode, and the power generating unit 21 is connected to the main body of the wearable device via the electrode.

The bio-battery as the power generating unit 21 that generates a potential difference by chemical reaction generates electricity by utilizing a sugar component supplied through a capillary of the user, for example. The connection between the power generating unit 21 and the capillary may be made by a noninvasive capillary needle provided at the power generating unit 21, or may be made by contact of surfaces by simply the power generating unit 21 being disposed on the front surface or the back surface of the eyelid of the user or on the surface of a surrounding tissue.

Figure 6:
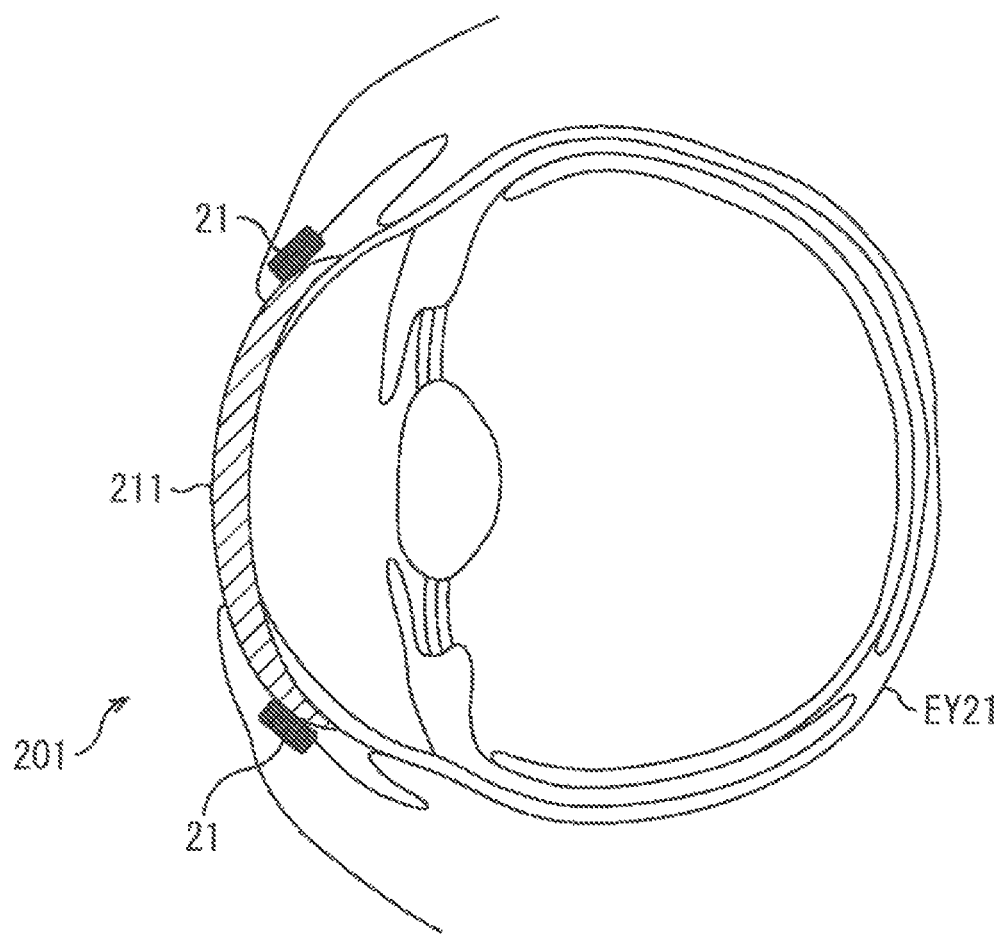
FIG. 6 is a diagram showing another configuration example of the wearable device.

When the power generating unit 21 thus generates electricity by utilizing the sugar component in the blood of the user supplied from the capillary, the wearable device is configured in a manner shown in FIG. 6, for example. In FIG. 6, portions corresponding to those in FIG. 2 are marked with the same reference numerals, and a description thereof is omitted as appropriate.

FIG. 6 is in a state where a contact lens-type wearable device 201 is worn on an eyeball EY21 so as to cover the entire cornea.

The wearable device 201 is in a shape that can be put on and taken off the eyeball EY21 of the user, like what is called a contact lens.

The wearable device 201 is composed of a main body 211 that is to be worn on the eyeball EY21 and the power generating unit 21 that is attachable to and detachable from the main body 211. In this example, the power generating unit 21 is fixed between the eyeball EY21 and the eyelid so as to be in contact with the back side of the eyelid of the user. The power generating unit 21 is connected to a portion near the outer periphery of the main body 211 via a not-illustrated electrode provided on the surface of the power generating unit 21 and a not-illustrated electrode provided on the surface of the main body 211.

In this example, the electricity storage element 22 is provided in the interior of the main body 211, and the functional configuration of the main body 211 is a configuration in which the power generating unit 21 is excluded from the wearable device 11 shown in FIG. 3, for example. That is, the main body 211 is composed of the regulator 61 to the power managing unit 63, the electricity storage element 22, the processing circuit 52, and the input/output unit 53.

Blood is supplied to the power generating unit 21 from a capillary existing in the eyelid of the user via a noninvasive capillary needle provided at the power generating unit 21, for example. Then, the power generating unit 21 generates electric power by chemical reaction with a sugar component contained in the supplied blood, and supplies electric power to the electricity storage element 22 provided in the interior of the main body 211 via a not-illustrated electrode to cause the electric power to be stored. In more detail, for example, electric power (charge) is supplied to the electricity storage element 22 via the regulator 61 and the charging circuit 62.

In this example, since electricity generation is performed by the supply of blood from the capillary and electric power is supplied at all times from the power generating unit 21 to the main body 211, electric power is supplied still more stably than in the embodiments described above.

Therefore, when the wearable device 201 performs its function in the range of the generated electric power, the electricity storage element 22 may not necessarily be provided in the wearable device 201. Since the sugar component is contained in a large amount in the blood, which is a body fluid, the power generating unit 21 can generate particularly large electric power in generating electricity using a body fluid or a secretion of the user as fuel.

Thus, by the wearable device 201, electric power can be generated by the sugar component contained in the blood of the user, and electric power can be supplied to each part as necessary and electricity can be stored. Therefore, electric power can be obtained without causing the user to be conscious of electricity supply to the wearable device 201, and the stress on the user in relation to electricity supply can be reduced. In addition, since electric power can be stably obtained by the blood, the user does not need to perform charging actions oneself.

When the enzyme of the bio-battery as the power generating unit 21 has deteriorated, the enzyme of the bio-battery may be loaded by eyedropping, or the power generating unit 21 itself may be detached from the wearable device 201 to be exchanged.

In the wearable device 201, the change in a component in the blood may be monitored from the electric power obtained by the component in the blood of the user. In such a case, similarly to the case described with reference to FIG. 3, the A/D conversion unit 71 converts the electricity generation amount in the power generating unit 21 to a digital value, and supplies the value to the processing unit 81, for example. The processing unit 81 finds the concentration value of the sugar component contained in the blood of the user from the value obtained in the A/D conversion unit 71, and causes the concentration value to be recorded in the recording unit 82.

Furthermore, in the example of FIG. 6, also electricity generation from a sugar component contained in the tear is possible at the same time as electricity generation from the blood. That is, when a structure in which sugar-enzyme reaction can be produced also on the surface of the power generating unit 21 disposed on the back side of the eyelid is employed, electricity generation can be performed in the power generating unit 21 using not only the blood but also the tear as fuel. In other words, electricity generation can be performed using both the blood and the tear as fuel, and a larger electric power amount can be obtained.

(Modification Example 1 of the Third Embodiment)
(Configuration Example of the Wearable Device)

Although an example in which the electricity storage element 22 is provided in the interior of the main body 211 of the wearable device 201 is described in FIG. 6, the electricity storage element 22 may be provided outside the main body 211.

Figure 7:
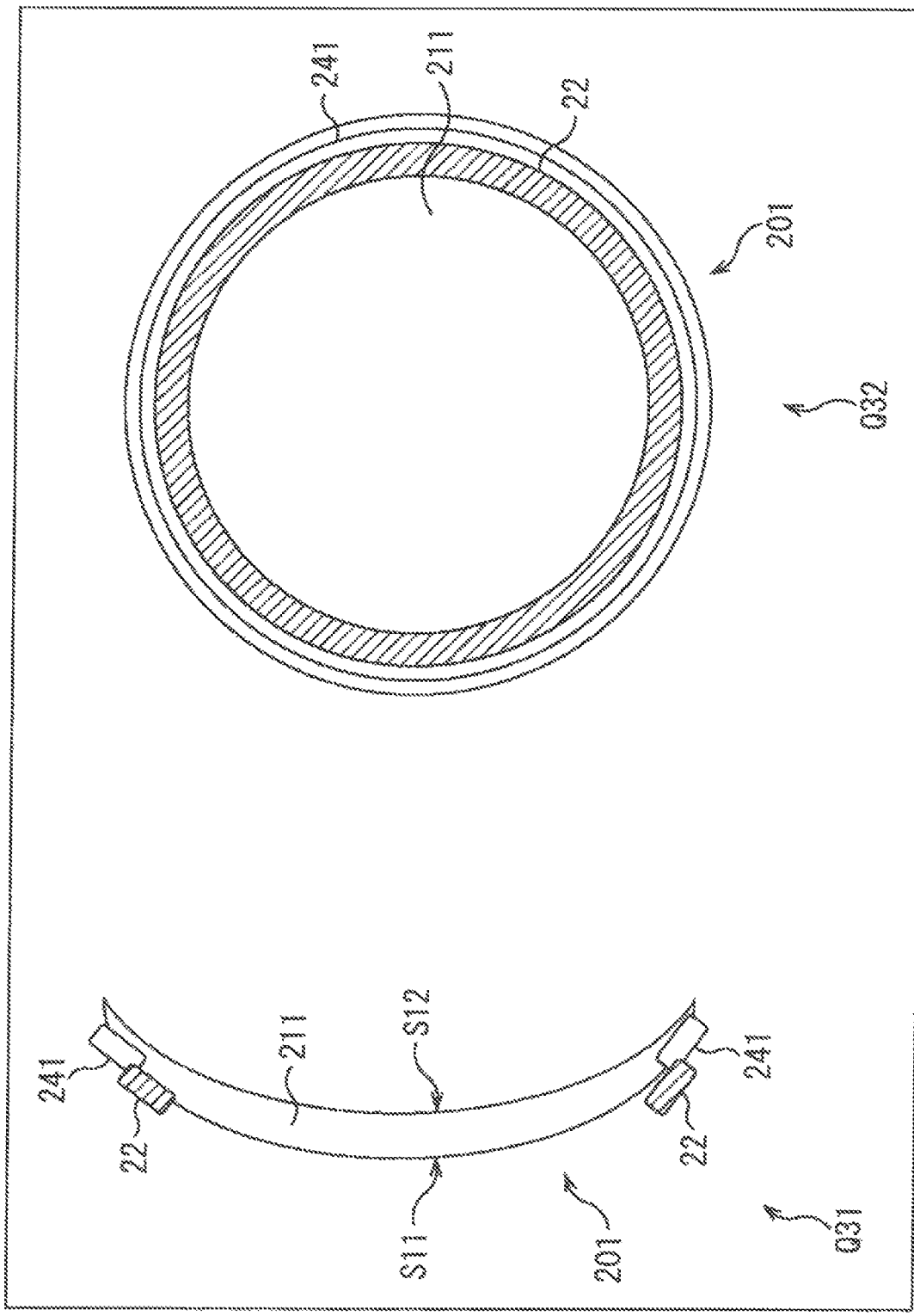
FIG. 7 is a diagram showing another configuration example of the wearable device.

In such a case, the wearable device 201 is configured in a manner shown in FIG. 7, for example. In FIG. 7, portions corresponding to those in FIG. 2 or FIG. 6 are marked with the same reference numerals, and a description thereof is omitted as appropriate. The wearable device 201 shown in FIG. 7 is in a state where the power generating unit 21 is detached from the wearable device 201, and the power generating unit 21 is not illustrated.

In FIG. 7, the drawing of the wearable device 201 shown by arrow Q31 shows a cross-sectional view when the wearable device 201 is viewed from the side surface side.

In this example, in the drawing of the main body 211 in the wearable device 201, the surface on the left side is the external world-side surface S11 that is located on the opposite side to the eyeball side when the user wears the wearable device 201, and the surface S12 facing the the eyeball side is the eyeball-side surface.

An electrode 241 is provided on the surface S11 of the main body 211 along the outer periphery of the main body 211, and the electricity storage element 22 is provided along the electrode 241 on the inside of the electrode 241, that is, on the center side of the surface S11.

When the wearable device 201 shown by arrow Q31 is viewed in the direction from the left side to the right side in the drawing, as shown by arrow Q32, the electrode 241 and the electricity storage element 22 are provided in an end portion of the main body 211 forming the wearable device 201. The drawing shown by arrow Q32 shows a view when the wearable device 201 is viewed from the same direction as when the user wearing the wearable device 201 is viewed from the front side.

In the wearable device 201 shown by arrow Q32, the electrode 241 and the electricity storage element 22 are provided along the end (outer periphery) of the main body 211; and these elements are located outside the visual field of the user wearing the wearable device 201, or are located such that the influence on the visual field is in a range acceptable to the user.

In this example, the power generating unit 21 is connected to the electrode 241, and electric power is supplied to the electricity storage element 22 from the power generating unit 21 via the electrode 241, the not-illustrated regulator 61, and the not-illustrated charging circuit 62, and is stored.

(Modification Example 2 of the Third Embodiment)
(Configuration Example of the Wearable Device)

In the wearable device 201, the power generating unit 21 and the electricity storage element 22 may be configured to be attachable to and detachable from the main body 211.

Figure 8:
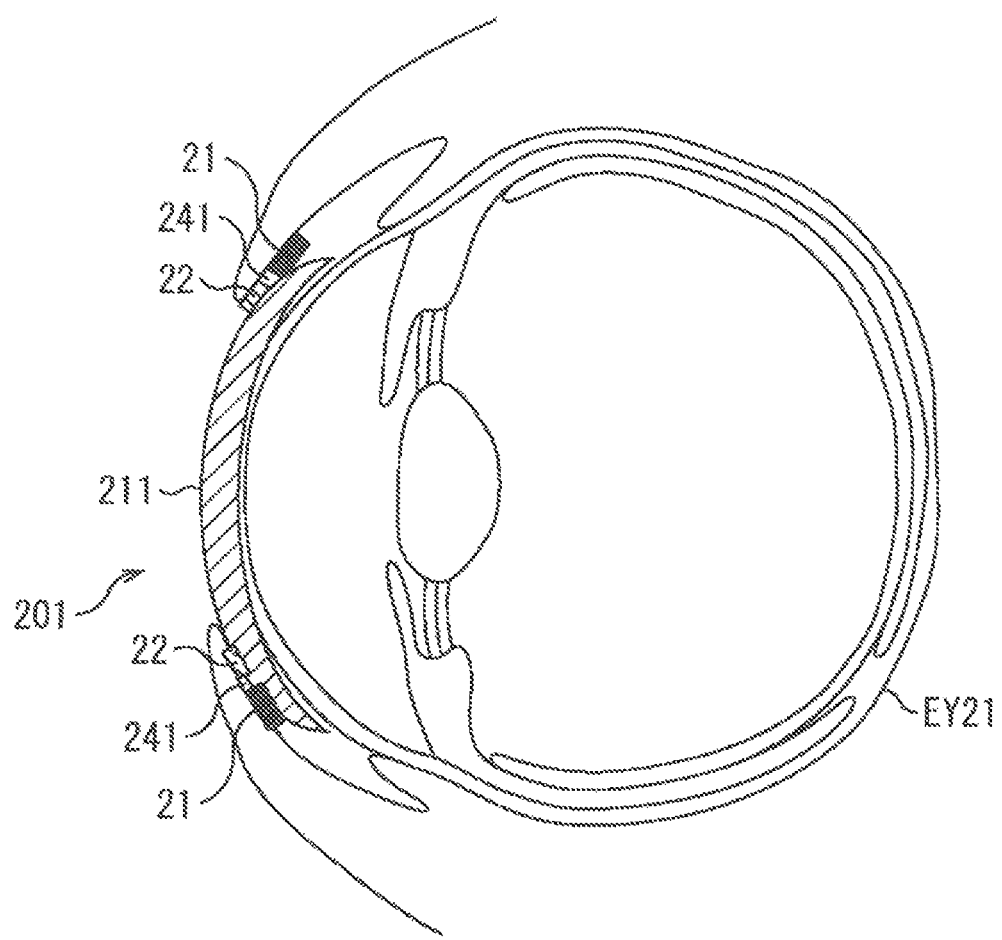
FIG. 8 is a diagram showing another configuration example of the wearable device.

In such a case, the wearable device 201 is configured in a manner shown in FIG. 8, for example. In FIG. 8, portions corresponding to those of FIG. 6 or FIG. 7 are marked with the same reference numerals, and a description thereof is omitted as appropriate.

In the example of FIG. 8, the main body 211 of the wearable device 201 is worn on the eyeball EY21 of the user, and the power generating unit 21 and the electricity storage element 22 are connected to an outer peripheral portion of the external world-side surface of the main body 211 via the electrode 241.

That is, the power generating unit 21, the electricity storage element 22, and the electrode 241 are configured integrally, and the power generating unit 21, the electricity storage element 22, and the electrode 241 are attachable to and detachable from the main body 211.

The power generating unit 21 is fixed to the back side of the eyelid of the user, and blood is supplied to the power generating unit 21 from a capillary existing in the eyelid of the user via a noninvasive capillary needle. The power generating unit 21 generates electric power by chemical reaction with a sugar component contained in the supplied blood, and supplies electric power to the electricity storage element 22 via the electrode 241, the not-illustrated regulator 61, and the not-illustrated charging circuit 62 to cause the electric power to be stored.

The electrode 241 and the electricity storage element 22 may be provided to be superposed on the surface of the power generating unit 21.

(Fourth Embodiment)
(Configuration Example of the Wearable Device)

Also a configuration in which the wearable device is provided with a capillary needle that penetrates from the external world-side surface to the eyeball-side surface of the contact lens-type wearable device and is sufficiently noninvasive to the cornea covering the aqueous humor, and electricity generation is performed by the power generating unit 21 using the aqueous humor as fuel is possible.

In this case, for example, the power generating unit 21 is a bio-battery that generates a potential difference by chemical reaction, or the like. By the capillary needle provided in the wearable device, aqueous humor is supplied from the anterior chamber to the power generating unit 21 through the cornea.

The power generating unit 21 generates electricity using a sugar component contained in the aqueous humor supplied from the capillary needle. Since aqueous humor is supplied to the power generating unit 21 at all times, stable electricity generation can be performed. Electric power can be obtained more stably than in the examples of the first embodiment and the second embodiment described above, and there is no need to provide an electrode on the surface of the wearable device like the third embodiment.

In the case where the power generating unit 21 thus generates electricity by utilizing a sugar component of the aqueous humor supplied from the anterior chamber, the wearable device is configured in a manner shown in FIG. 9, for example. In FIG. 9, portions corresponding to those in FIG. 2 are marked with the same reference numerals, and a description thereof is omitted as appropriate.

In FIG. 9, the drawing of the wearable device 11 shown by arrow Q41 shows a cross-sectional view when the wearable device 11 is viewed from the side surface side.

In this example, in the drawing of the wearable device 11, the surface on the left side is the external world-side surface S11, and the surface S12 facing the the eyeball side is the eyeball-side surface.

The electricity storage element 22 is provided on the external world-side surface S11 of the wearable device 11 along the outer periphery of the wearable device 11, and the power generating unit 21 is provided on the eyeball-side surface S12 of the wearable device 11 along the outer periphery of the wearable device 11.

When the wearable device 11 shown by arrow Q41 is viewed in the direction from the left side to the right side in the drawing, as shown by arrow Q42, the electricity storage element 22 is provided near the end of the wearable device 11. The drawing shown by arrow Q42 shows a view when the wearable device 11 is viewed from the same direction as when the user wearing the wearable device 11 is viewed from the front side, that is, a front view of the wearable device 11.

In the wearable device 11 shown by arrow Q42, the electricity storage element 22 is provided along the end (outer periphery) of the wearable device 11; and the power generating unit 21 and the electricity storage element 22 are located outside the visual field of the user wearing the wearable device 11 or are located such that the influence on the visual field is in a range acceptable to the user.

Thus, in the wearable device 11 shown in FIG. 9, the arrangement positions of the power generating unit 21 and the electricity storage element 22 are different from those in the wearable device 11 shown in FIG. 2. Furthermore, while the wearable device 11 of FIG. 2 generates electricity by utilizing tears, the wearable device 11 of FIG. 9 generates electricity by utilizing aqueous humor.

In the example of FIG. 9, in a state where the wearable device 11 is worn on the eyeball of the user, the power generating unit 21 generates electricity using a sugar component contained in the aqueous humor supplied from a capillary needle that is provided at the power generating unit 21 and is disposed on the cornea, for example. That is, the sugar component of the aqueous humor is utilized as fuel for the bio-battery as the power generating unit 21.

Upon being supplied with aqueous humor, the power generating unit 21 generates electric power by chemical reaction with a sugar component contained in the aqueous humor. The generated electric power is supplied to each part of the wearable device 11, and is supplied to and stored in the electricity storage element 22, as appropriate. In more detail, for example, electric power is supplied from the power generating unit 21 to the electricity storage element 22 via the regulator 61 and the charging circuit 62, and is stored.

In a state where the wearable device 11 is worn on the user, since aqueous humor is always supplied to the power generating unit 21 by the capillary needle, electric power is stably supplied to each part of the wearable device 11. That is, when the wearable device 11 performs its function in the range of the generated electric power, the electricity storage element 22 may not necessarily be provided in the wearable device 11.

Thus, by the wearable device 11, when the user wears the wearable device 11, electric power can be generated by the aqueous humor of the user, and electric power can be supplied to each part as necessary and electricity can be stored.

Therefore, electric power can be obtained without causing the user to be conscious of electricity supply to the wearable device 11, and the stress on the user in relation to electricity supply can be reduced. In addition, since electric power can be stably obtained by the aqueous humor, the user does not need to perform charging actions oneself.

When the enzyme of the bio-battery as the power generating unit 21 has deteriorated, the enzyme of the bio-battery may be loaded by eyedropping or by taking off the wearable device 11 itself, or the wearable device 11 itself may be exchanged for a new one.

In the wearable device 11, the change in a component in the aqueous humor may be monitored from the electric power obtained by the component in the aqueous humor of the user. In such a case, similarly to the case described with reference to FIG. 3, the A/D conversion unit 71 converts the electricity generation amount in the power generating unit 21 to a digital value, and supplies the value to the processing unit 81, for example. The processing unit 81 finds the concentration value of the sugar component contained in the aqueous humor of the user from the value obtained in the A/D conversion unit 71, and causes the concentration value to be recorded in the recording unit 82.

Furthermore, in the example of FIG. 9, also electricity generation from a sugar component contained in the tear is possible at the same time as electricity generation from the aqueous humor. That is, when a structure in which sugar-enzyme reaction can be produced also on the surface of the power generating unit 21 disposed on the eyeball-side surface is employed, electricity generation can be performed in the power generating unit 21 using not only the aqueous humor but also the tear as fuel. In other words, electricity generation can be performed using both the aqueous humor and the tear as fuel, and a larger electric power amount can be obtained.

(Modification Example 1 of the Fourth Embodiment)
(Configuration Example of the Wearable Device)

Although an example in which the power generating unit 21 that generates electricity by utilizing a sugar component of the aqueous humor supplied from the anterior chamber is provided on the eyeball-side surface S12 of the wearable device 11 is described in the fourth embodiment, the power generating unit 21 may be provided in other positions.

Specifically, for example as shown in FIG. 10, the power generating unit 21 may be provided so as to cover both the eyeball-side surface S12 and the external world-side surface S11 along the outer periphery of the wearable device 11. In FIG. 10, portions corresponding to those in FIG. 9 are marked with the same reference numerals, and a description thereof is omitted as appropriate.

In FIG. 10, the drawing of the wearable device 11 shown by arrow Q51 shows a cross-sectional view when the wearable device 11 is viewed from the side surface side.

In this example, in the drawing of the wearable device 11, the surface on the left side is the external world-side surface S11, and the surface S12 facing the the eyeball side is the eyeball-side surface.

The power generating unit 21 is provided on the external world-side surface S11 and the eyeball-side surface S12 of the wearable device 11 so as to cover the edge of the wearable device 11 along the outer periphery. The electricity storage element 22 is provided on the external world-side surface S11 of the wearable device 11 along the outer periphery of the wearable device 11.

When the wearable device 11 shown by arrow Q51 is viewed in the direction from the left side to the right side in the drawing, as shown by arrow Q52, the power generating unit 21 is provided in an end portion of the wearable device 11, and the electricity storage element 22 is provided adjacent to the inside of the power generating unit 21. The drawing shown by arrow Q52 shows a view when the wearable device 11 is viewed from the same direction as when the user wearing the wearable device 11 is viewed from the front side, that is, a front view of the wearable device 11.

In the wearable device 11 shown by arrow Q52, the power generating unit 21 and the electricity storage element 22 are provided at the end (outer periphery) of the wearable device 11; and these elements are located outside the visual field of the user wearing the wearable device 11, or are located such that the influence on the visual field is in a range acceptable to the user.

In the example of FIG. 10, a noninvasive capillary needle is provided on the surface on the cornea side of the power generating unit 21 or the like, and aqueous humor is supplied to the power generating unit 21 by the capillary needle. Then, the power generating unit 21 generates electricity using a sugar component contained in the aqueous humor supplied from the capillary needle. That is, upon being supplied with aqueous humor, the power generating unit 21 generates electric power by chemical reaction with a sugar component contained in the aqueous humor. The generated electric power is supplied to each part of the wearable device 11, and is supplied to and stored in the electricity storage element 22, as appropriate. In more detail, for example, electric power is supplied from the power generating unit 21 to the electricity storage element 22 via the regulator 61 and the charging circuit 62, and is stored.

Also in the wearable devices of the other embodiments described above, the power generating unit 21 may be provided on both the external world-side surface and the eyeball-side surface of the wearable device so as to run along the outer periphery of the wearable device and cover its edge.

(Fifth Embodiment)
(Configuration Example of the Electricity Supply System)

The contact lens-type wearable device described above is, in a state of not being worn on the eyeball of the user, preferably stored in a storage case or the like and stored in a liquid for keeping hygiene, similarly to a contact lens, for example.

In the case where the wearable device is put in a storage case and stored in a liquid, when a liquid that acts on the power generating unit 21 is used as the storage liquid, not only can the wearable device be stored hygienically by the storage case, but various functions can also be provided.

For example, in the case where the power generating unit 21 of the wearable device is a bio-battery that generates a potential difference by chemically reacting a sugar and an enzyme, by putting in the sugar as a component of the storage liquid of the storage case, charging can be performed while the wearable device is stored in the storage case. In such a case, an electricity supply system composed of the wearable device and the storage case is configured in a manner shown in FIG. 11, for example.

In the electricity supply system shown in FIG. 11, a wearable device 271-1 and a wearable device 271-2 that are to be worn on the left and right eyes of a user are stored in a storage case 272. The wearable device 271-1 and the wearable device 271-2 are the wearable device described in any one of the embodiments described above, and include the power generating unit 21 and the electricity storage element 22. The power generating unit 21 is a bio-battery that generates a potential difference by chemically reacting a sugar and an enzyme, or the like, for example.

Hereinafter, when there is no particular need to distinguish the wearable device 271-1 and the wearable device 271-2, they may be referred to as simply a wearable device 271.

The storage case 272 is composed of a case body 281 and a lid 282 that covers the opening of the case body 281, and an ultrasonic vibrating base 283-1 and an ultrasonic vibrating base 283-2 for holding the wearable device 271 are provided in the case body 281.

The wearable device 271-1 is placed on the ultrasonic vibrating base 283-1, and the wearable device 271-2 is placed on the ultrasonic vibrating base 283-2; and these wearable devices 271 are in a state of being immersed in a storage liquid that is fully put in the case body 281. That is, the case body 281 is in a shape allowing the storage liquid to be retained such that the wearable device 271 is in a state of being impregnated with the storage liquid.

The storage liquid is a liquid containing a sugar component serving as the fuel of the power generating unit 21; and when the wearable device 271 is stored in the storage case 272 in a state of being immersed in the storage liquid as shown in FIG. 11, the enzyme of the power generating unit 21 and the sugar component of the storage liquid chemically react to generate electric power. The electric power generated by the power generating unit 21 is supplied to the electricity storage element 22 via the not-illustrated regulator 61 and the not-illustrated charging circuit 62, and is stored in the electricity storage element 22.

Therefore, by the electricity supply system shown in FIG. 11, the user can perform charging by simply storing the wearable device 271 in the storage case 272, and can operate the wearable device 271 as soon as the wearable device 271 is taken out of the storage case 272.

In this example, since the action of the user's storing the wearable device 271 and the action of charging the wearable device 271 are carried out as one, the user does not need to be particularly conscious of the action of charging. Thereby, the stress on the user in relation to electricity supply to the wearable device 271 can be reduced.

Hereinafter, when there is no particular need to distinguish the ultrasonic vibrating base 283-1 and the ultrasonic vibrating base 283-2, they may be referred to as simply an ultrasonic vibrating base 283.

In the electricity supply system shown in FIG. 11, also functions of cleaning the wearable device 271 and refreshing the power generating unit 21, and performing data communication during the storage of the wearable device 271 can be achieved. Furthermore, an electricity storage element may be provided in the storage case 272 so that electric power can be supplied to the wearable device 271 from the electricity storage element via an electrode, as necessary. In such a case, the electricity storage element may be charged beforehand by an alternating current (AC) power source, or a power generating unit that generates electricity by reaction with a liquid may be provided separately in the case body 281 of FIG. 11 so that the electricity storage element is charged by the power generating unit, for example.

The ultrasonic vibrating base 283 can, by applying vibration to the wearable device 271 that it holds, ultrasonically clean the surface of the wearable device 271, and in addition, stir a liquid such as the storage liquid existing in the path of supplying the liquid to the surfaces etc. of the power generating unit 21 and other power generating units provided in the case body 281 etc., exchange the liquid that has reacted with the power generating unit 21 etc. for an unreacted liquid with good efficiency, and wash away the old enzyme loaded in the power generating unit 21 of the wearable device 271, for example. At this time, when an enzyme is contained as a component of the storage liquid, a new enzyme contained in the storage liquid can be loaded in the power generating unit 21. That is, by vibrating the wearable device 271 using the ultrasonic vibrating base 283, the power source function of the power generating unit 21 can be refreshed, and the electricity generation efficiency can be improved.

The ultrasonic vibrating base 283-1 is provided with a terminal 291-1 for data transfer and reception, and similarly the ultrasonic vibrating base 283-2 is provided with a terminal 291-2 for data transfer and reception. Hereinafter, when there is no particular need to distinguish the terminal 291-1 and the terminal 291-2, they may be referred to as simply a terminal 291.

The external device 41 shown in FIG. 3 or FIG. 4 is provided in the case body 281, and the communication module 101 of the external device 41 communicates with the not-illustrated communication module 96 of the wearable device 271 via the terminal 291.

For example, in a state where the wearable device 271 is held by the ultrasonic vibrating base 283, the external device 41 reads information from the wearable device 271 via the terminal 291, and transfers and receives data for the updating of the program recorded in the recording unit 82 etc.

Thus, when data transfer and reception are performed between the wearable device 271 and the external device 41 in a state where the wearable device 271 is stored in the storage case 272, it is necessary for the electric power to be stable in the wearable device 271. However, in this example, a storage liquid in which a sugar component is contained at a certain concentration or more may be used as the storage liquid that is fully put in the case body 281; thereby, electric power can be stably supplied to the wearable device 271 even during data transfer and reception. For the case where electric power is not sufficient, a configuration in which electric power during communication is supplied from the storage case 272 to the wearable device 271 through an electrode for communication or some other electrode may be employed.

Although an example in which the external device 41 is provided in the case body 281 is described in this embodiment, also a configuration in which the storage case 272 and the external device 41 are connected and the external device 41 is connected to the wearable device 271 via the storage case 272 is possible. In such a case, the wearable device 271 and the external device 41 perform communication and data transfer and reception via the terminal 291. Although an example in which the wearable device 271 is held by the ultrasonic vibrating base 283 is described here, the base that holds the wearable device 271 in the case body 281 may not have a vibrating function, and in particular the base that holds the wearable device 271 may not be provided.

The embodiment of the present technology is not limited to the embodiments described above, and various alterations are possible without departing from the spirit of the present technology.

Additionally, the present technology may also be configured as below.

[1]

A wearable device wearable on an eyeball, including:

a power generating unit configured to generate electric power by chemical reaction with a substance supplied from an outside; and a power managing unit configured to supply electric power obtained in the power generating unit to each part.

[2]

The wearable device according to [1], wherein the power generating unit generates electric power by chemical reaction with the substance contained in a secretion or a body fluid of a user wearing the wearable device.

[3]
The wearable device according to [2], wherein the substance is a sugar.

[4]
The wearable device according to [2] or [3], further including
an electricity storage unit configured to store electric power obtained in the power generating unit.

[5]
The wearable device according to any one of [2] to [4], wherein the power generating unit is provided on a surface on an opposite side to the eyeball side of the wearable device and generates electric power by chemical reaction with the substance contained in a tear as the secretion.

[6]
The wearable device according to any one of [2] to [5], wherein the power generating unit is provided on a film attachable to and detachable from the wearable device.

[7]
The wearable device according to any one of [2] to [4], wherein the power generating unit is located on a front surface of an eyelid of the user, a back surface of an eyelid of the user, or a surface of a tissue around an eye of the user when the wearable device is worn on the user.

[8]
The wearable device according to [7], wherein the power generating unit is attachable to and detachable from the wearable device.

[9]
The wearable device according to [7] or [8], wherein the power generating unit generates electric power by chemical reaction with the substance contained in at least one of blood and aqueous humor as the body fluid.

[10]
The wearable device according to any one of [2] to [4], wherein the power generating unit is provided so as to cover an outer periphery of the wearable device.

[11]
The wearable device according to any one of [2] to [10], further including
a processing unit configured to perform processing in accordance with a concentration of the substance supplied to the power generating unit.

[12]
The wearable device according to any one of [2] to [10], further including
a processing unit configured to monitor a change in the substance contained in the secretion or the bodily fluid of the user supplied to the power generating unit.

[13]
The wearable device according to [12], wherein the processing unit estimates health condition or stress condition of the user on the basis of a monitoring result of a change in the substance.

[14]
An electricity supply system including:
a wearable device wearable on an eyeball; and
a storage case configured to store the wearable device, the wearable device including
a power generating unit configured to generate electric power by chemical reaction with a substance supplied from an outside,
a power managing unit configured to supply electric power obtained in the power generating unit to each part, and
an electricity storage unit configured to store electric power obtained in the power generating unit,
wherein the storage case is capable of retaining a storage liquid containing the substance in such a manner that the wearable device is in a state of being impregnated with the storage liquid.

REFERENCE SIGNS LIST 11 wearable device
21 power generating unit
22 electricity storage element
81 processing unit
96 communication module
161 wearable device
172 film
201 wearable device
241 electrode
271-1, 271-2, 271 wearable device
272 storage case

The invention claimed is:
1. A wearable device, comprising:
a main body, wherein
the main body comprises an exterior side and an interior side, and
the wearable device is mountable on an eyeball of a user from the interior side of the main body;
a film that is one of attachable to the exterior side of the main body or detachable from the exterior side of the main body;
an enzyme on the film; and
first circuitry on the film, wherein the first circuitry is configured to:
receive one of a sugar or a sugar component associated with the user;
generate electric power based on a chemical reaction of the enzyme with one of the received sugar or the received sugar component; and
supply the generated electric power to the main body.
2. The wearable device according to claim 1, wherein one of the received sugar or the received sugar component is contained in one of a secretion fluid of the user or a body fluid of the user.
3. The wearable device according to claim 2, wherein the first circuitry is further configured to store the generated electric power.
4. The wearable device according to claim 2, wherein the secretion fluid is a tear of the user.
5. The wearable device according to claim 2, wherein the body fluid is at least one of blood or aqueous humor.
6. The wearable device according to claim 2, wherein the first circuitry covers an outer periphery of the film.
7. The wearable device according to claim 2, wherein the main body further comprises second circuitry configured to:
determine a concentration value of one of the received sugar or the received sugar component; and
store the determined concentration value.
8. The wearable device according to claim 2, wherein the main body further comprises second circuitry configured to monitor a change in a concentration of one of the sugar or the sugar component.

* * * * *